United States Patent
Gribbons et al.

(10) Patent No.: US 6,893,417 B2
(45) Date of Patent: May 17, 2005

(54) CATHETER AND GUIDE WIRE EXCHANGE SYSTEM WITH IMPROVED PROXIMAL SHAFT AND TRANSITION SECTION

(75) Inventors: Richard Gribbons, Galway (IE); John MacNamara, Galway (IE); Niall Duffy, Galway (IE); Ash Varma, Galway (IE); Gerry Clarke, Galway (IE); Mark Casley, Galway (IE); Noel Coyle, Galway (IE); David Quinn, Galway (IE); Rodney Bell, Galway (IE); Kevin Boyle, Galway (IE); Kevin Treacy, Galway (IE); Patrick Duane, Galway (IE); Paula McDonnell, Galway (IE); Declan Costello, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/720,535

(22) Filed: Nov. 24, 2003

(65) Prior Publication Data

US 2004/0122363 A1 Jun. 24, 2004

Related U.S. Application Data

(63) Continuation-in-part of application No. 10/251,477, filed on Sep. 20, 2002.

(60) Provisional application No. 60/479,695, filed on Jun. 19, 2003.

(51) Int. Cl.$^7$ .............................................. A61M 31/00
(52) U.S. Cl. .................................................. 604/103.04
(58) Field of Search ................................. 604/509–510, 604/95.03, 95.04, 96.01–97.02, 101.01–101.05, 102.01–102.03, 103–103.04, 104, 164.1, 523–525, 915, 917, 919; 606/191–199; 623/1.1, 1.11, 1.12, 1.15

(56) References Cited

U.S. PATENT DOCUMENTS

| | | |
|---|---|---|
| 5,334,187 A | 8/1994 | Fischell et al. |
| 5,718,680 A | 2/1998 | Horzewski et al. |
| 2003/0191491 A1 * | 10/2003 | Duane et al. ............... 606/194 |

* cited by examiner

Primary Examiner—Nicholas D. Lucchesi
Assistant Examiner—Michael M Thompson

(57) ABSTRACT

A catheter and guide wire exchange system including a catheter that has a guide wire lumen with a guide way extending along a length of the proximal shaft. A guide member is slidably disposed about the proximal shaft for directing a guide wire into or out of the guide way and the guide wire lumen. A transition section joins the trilumen proximal shaft to a coaxial distal shaft.

7 Claims, 10 Drawing Sheets

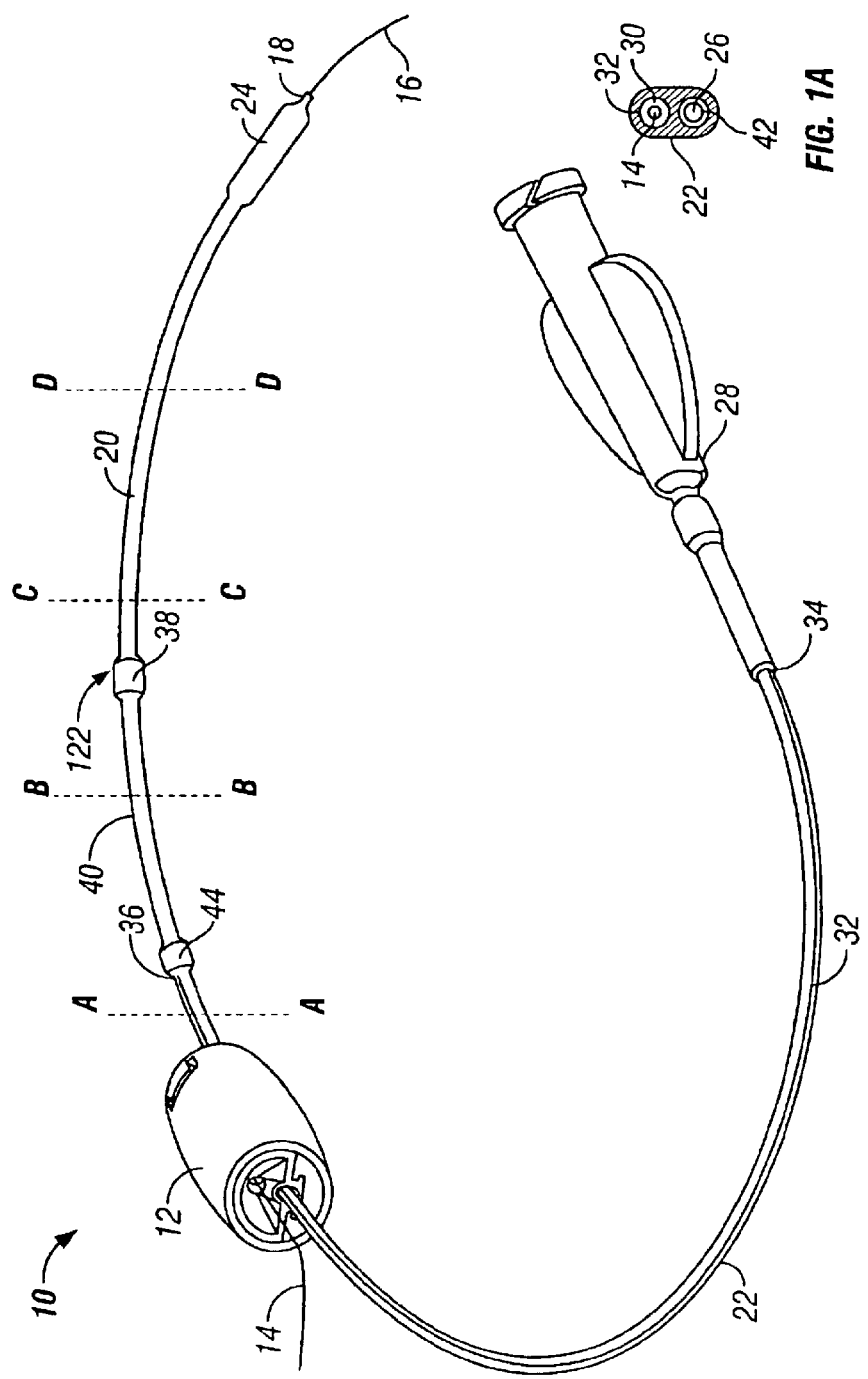

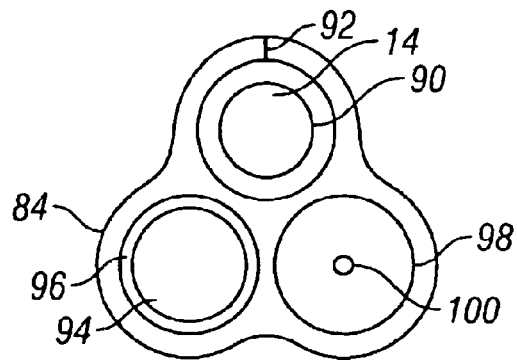
FIG. 4A
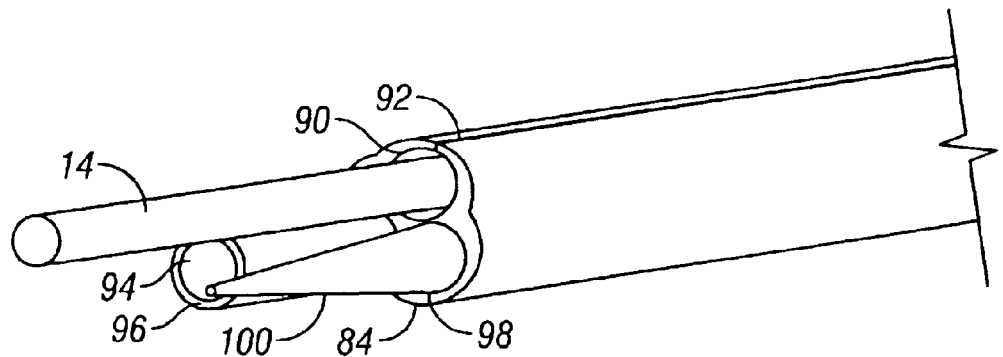
FIG. 4B
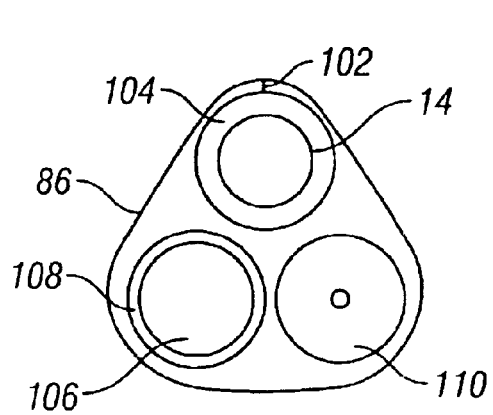
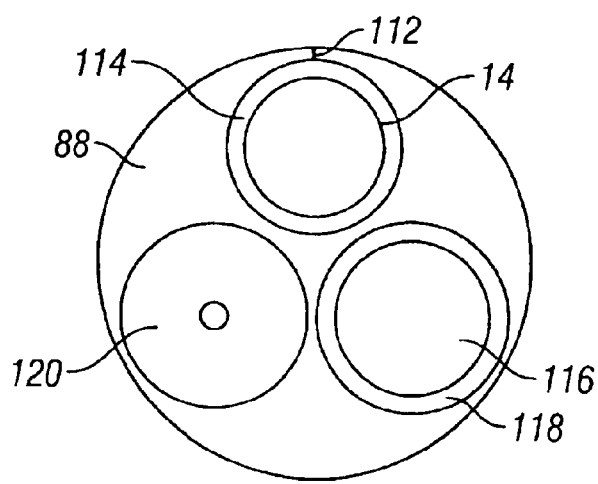
FIG. 4C  FIG. 4D

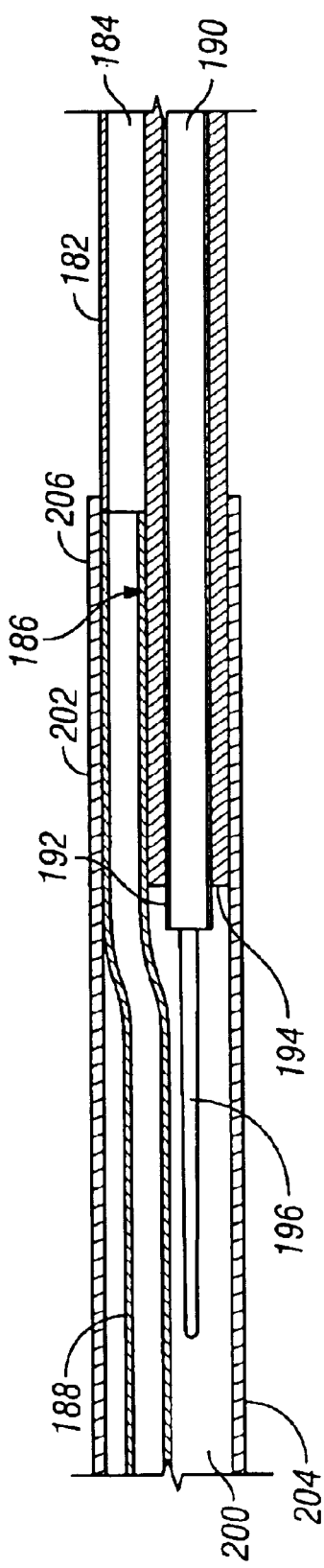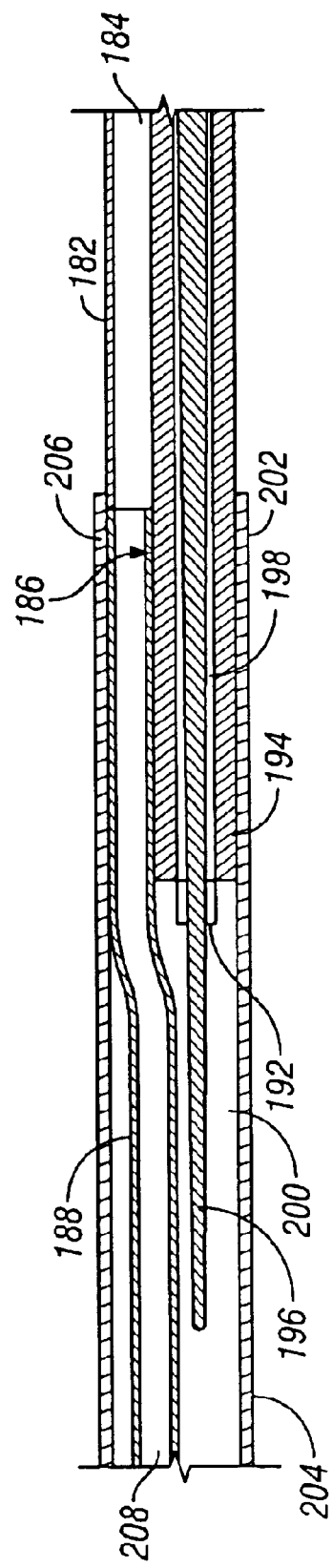

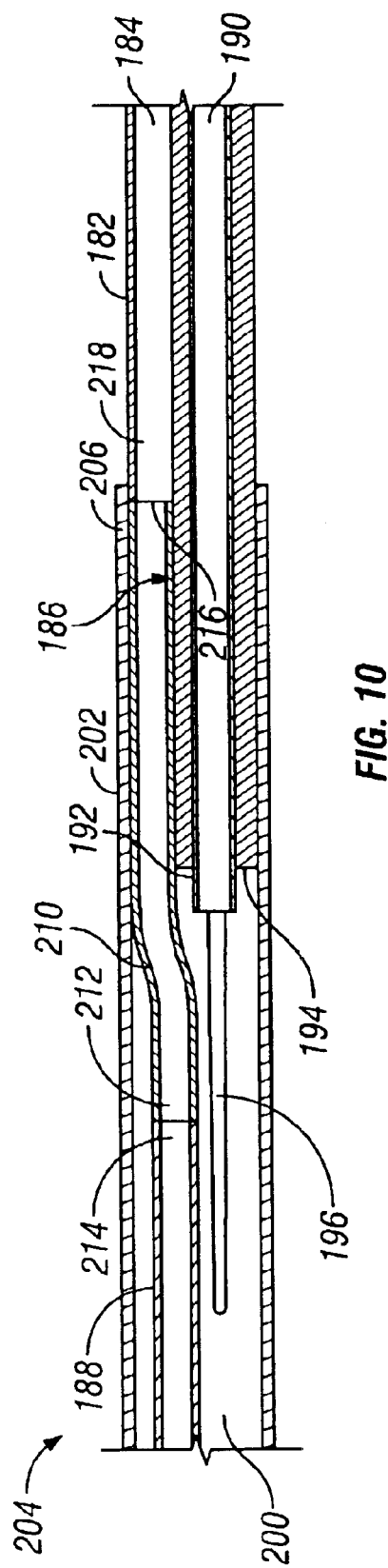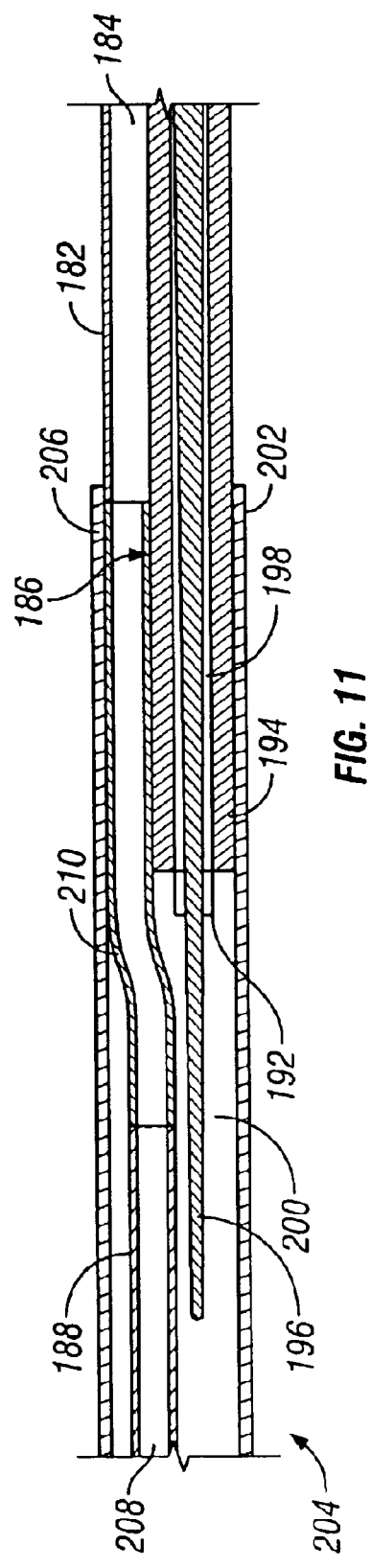

CATHETER AND GUIDE WIRE EXCHANGE SYSTEM WITH IMPROVED PROXIMAL SHAFT AND TRANSITION SECTION

CONTINUATION DATA

This application is a continuation in part of U.S. application Ser. No. 10/251477, filed Sep. 20, 2002, and claims the benefit of Provisional application Ser. No. 60/479,695, filed Jun. 19, 2003.

FIELD OF THE INVENTION

The present invention relates to catheters used in the vascular system and more particularly to a system for facilitating exchange of such catheters and guide wires, and for using such catheters and guide wires to access selected sites within a patient.

BACKGROUND OF THE INVENTION

Catheters are inserted to various locations within a patient for a wide variety of purposes and medical procedures. For example only, one type of catheter is used in percutaneous catheter intervention (PCI) for the treatment of a vascular constriction termed a stenosis. In this instance, the catheter has a distally mounted balloon that can be placed, in a deflated condition, within the stenosis, and then inflated to dilate the narrowed lumen of the blood vessel. Such balloon dilation therapy is generally named percutaneous transluminal angioplasty (PTA). The designation PTCA, for percutaneous transluminal coronary angioplasty, is used when the treatment is more specifically employed in vessels of the heart. PTCA is used to open coronary arteries that have been occluded by a build-up of cholesterol fats or atherosclerotic plaque. The balloon at the distal end of the catheter is inflated, causing the site of the stenosis to widen.

The dilation of the occlusion, however, can form flaps, fissures and dissections, which may result in reclosure of the dilated vessel or even perforations in the vessel wall. Implantation of a stent can provide support for such flaps and dissections and thereby prevent reclosure of the vessel or provide a patch repair for a perforated vessel wall until corrective surgery can be performed. A stent is typically a cylindrically shaped device formed from wire(s) or a metal tube and is intended to act as a permanent prosthesis. A stent is deployed in a body lumen from a radially compressed configuration into a radially expanded configuration that allows it to contact and support a body lumen. A stent can be implanted during an angioplasty procedure by using a balloon catheter bearing a compressed stent that has been loaded onto the balloon. The stent radially expands as the balloon is inflated, forcing the stent into contact with the body lumen, thereby forming a supporting relationship with the lumen walls. Alternatively, self-expanding stents may be deployed with a sheath-based delivery catheter. Deployment is effected after the stent has been introduced percutaneously, transported transluminally and positioned at a desired location by the delivery catheter. In addition to angioplasty and stenting procedures, other therapeutic procedures require use of a delivery catheter, such as drug delivery, filters, occlusion devices, diagnostic devices and radiation treatment.

Typically, the placement of such therapeutic delivery catheters involves the use of a guide wire, which may be inserted into the patient's vasculature through the skin, and advanced to the location of the treatment site. The delivery catheter, which has a lumen adapted to receive the guide wire, then is advanced over the guide wire. Alternatively, the guide wire and the delivery catheter may be advanced together, with the guide wire protruding from the distal end of the delivery catheter. In either case, the guide wire serves to guide the delivery catheter to the location to be treated.

There are four general types of catheters: "over-the-wire" (OTW) catheters, Multi-Exchange catheters (MX) such as disclosed in U.S. Pat. No. 4,998,356 (Crittenden, et al.) and co-pending application U.S. Ser. No. 10/116,234, "rapid exchange" catheters and "fixed wire" or "a balloon on a wire" catheters. OTW and rapid exchange catheters require use of a guide wire separate from the catheter while a fixed wire or balloon on a wire catheter has an integral guide wire. An OTW catheter comprises a guide wire lumen that extends the entire length of the catheter. The guide wire is disposed entirely within the catheter guide wire lumen except for distal and proximal portions of the guide wire, which extend beyond the distal and proximal ends of the catheter respectively. An MX catheter has an over-the-wire configuration while the catheter is within the patient's body. Thus, the guide wire is disposed entirely within the catheter guide wire lumen, except for the distal and proximal portion of the guide wire, which extend beyond the distal and proximal ends of the catheter respectively when it is fully inserted into the patient.

OTW and MX catheters have many advantages traceable to the presence of the full length guide wire lumen, such as good stiffness and pushability for readily advancing the catheter through the tortuous vasculature and across tight stenosis. The full-length guide wire lumen permits removal and replacement of a guide wire in an indwelling catheter, as may be required to alter the shape of the guide wire tip. It is also sometimes desirable to exchange one guide wire for another guide wire having a different stiffness. For example, a relatively soft, or flexible guide wire may prove to be suitable for guiding a PTCA catheter through a particular tortuous anatomy, whereas following up with a stent delivery catheter through the same vasculature region may require a guide wire that is relatively stiffer.

Traditional over-the-wire catheters do suffer some shortcomings, however. For example, it often becomes necessary, in the performance of a PCI, to exchange one indwelling catheter for another catheter. In order to maintain a guide wire in position while withdrawing the catheter, the guide wire must be gripped at its proximal end to prevent it from being pulled out of the blood vessel with the catheter. For example, a PTCA catheter, which may typically be on the order of 135 centimeters long, is longer than the proximal portion of the standard guide wire that protrudes out of patient. Therefore, exchanging an over-the-wire PTCA catheter requires an exchange guide wire of about 300 centimeters long, whereas a standard guide wire is about 165 centimeters long.

In one type of over-the-wire catheter exchange, the standard length guide wire first is removed from the lumen of the indwelling catheter. Then, the longer exchange guide wire is passed through the catheter to replace the original wire. Next, while holding the exchange guide wire by its proximal end to control its position in the patient, the catheter is withdrawn proximally from the blood vessel over the exchange guide wire. After the first catheter has been removed, the next OTW catheter is threaded onto the proximal end of the exchange guide wire and is advanced along the exchange guide wire, through the guiding catheter, and into the patient's blood vessels until the distal end of the catheter is at the desired location. The exchange guide wire may be left in place or it may be exchanged for a shorter, conventional-length guide wire. In an alternative type of catheter exchange procedure, the length of the initial guide wire may be extended by way of a guide wire extension apparatus. Regardless of which exchange process is used, the very long exchange guide wire is awkward to handle, thus requiring at least two operators to perform the procedure.

A balloon catheter capable of both very fast exchange and simple guidewire and catheter exchange is particularly advantageous. A catheter designed to address this need sold by Medtronic Vascular of Santa Rosa, Calif. under the trademarks MULTI-EXCHANGE, ZIPPER MX, ZIPPER and/or MX is disclosed in U.S. Pat. No. 4,988,356 (Crittenden et al.) and pending U.S. applications Ser. No. 10/116,234 filed Apr. 4, 2003; Ser. No. 10/251578, filed Sep. 20, 2003 and Ser. No. 10/251477, filed Sep. 20, 2003, which are incorporated in their entirety herein by reference. A MX catheter includes a catheter shaft having a cut that extends longitudinally between the proximal end and the distal end of the catheter and that extends radially from the catheter shaft outer surface to the guide wire lumen. A guide member coupled to the catheter shaft functions to temporarily open the cut such that the guide wire may extend transversely into or out of the cut at any location along its length. By moving the proximal shaft through the guide member, the effective over-the-wire length of the MX catheter is adjustable.

When using the MX catheter, the guide wire is maneuvered through the patient's vascular system such that the distal end of the guide wire is positioned across the treatment site. With the guide member positioned near the distal end of the catheter, the proximal end of the guide wire is threaded into the guide wire lumen opening at the distal end of the catheter and through the guide member such that the proximal end of the guide wire protrudes out the proximal end of the guide member. By securing the guide member and the proximal end of the guide wire in a fixed position, the catheter may then be delivered over the guide wire by advancing the catheter toward the guide member. In doing so, the catheter advances through the guide member such that the guide wire lumen envelops the guide wire as the catheter is advanced into the patient's vasculature. In a PTCA embodiment, the MX catheter may be advanced over the guide wire in this manner until the distal end of the catheter having the dilatation balloon is positioned within the stenosis and essentially the entire length of the guide wire is encompassed within the guide wire lumen.

Furthermore, the indwelling MX catheter may be exchanged with another catheter by reversing the operation described above. To this end, the indwelling catheter may be removed by withdrawing the proximal end of the catheter from the patient while holding the proximal end of the guide wire and the guide member in a fixed position. When the catheter has been withdrawn to the point where the distal end of the cut has reached the guide member, the distal portion of the catheter over the guide wire is of a sufficiently short length that the catheter may be drawn over the proximal end of the guide wire without releasing control of the guide wire or disturbing its position within the patient. After the catheter has been removed, another MX catheter may be threaded onto the guide wire and advanced over the guide wire in the same manner described above with regard to the MX catheter. The MX catheter not only permits catheter exchange without the use of the very long exchange guide wire and without requiring withdrawal of the initially placed guide wire, but it also overcomes many of the other difficulties discussed in association with rapid exchange catheters described below.

Rapid exchange catheters developed in attempt to eliminate the need for a guide wire extension or exchange wires. Catheters of this type are formed so that the guide wire is located outside of the catheter except for a short guide wire lumen that extends within only a comparatively short distal segment of the catheter. The rapid exchange catheter's proximal exit port for the guide wire is typically located about 5 cm (2.0 in) to 30 cm (11.8 in) proximal to the catheter's distal end. In use, the guide wire is placed initially in the patient's vascular system. The distal segment of the rapid exchange catheter then is threaded onto the wire. The catheter can be advanced alongside the guide wire with its distal segment being attached to and guided along the guide wire. The rapid exchange catheter can be removed and exchanged for another rapid exchange catheter without the use of a very long exchange guide wire and without requiring withdrawal of the initially placed guide wire.

A difficulty associated with rapid exchange catheters is that it is not possible to exchange guide wires in an indwelling rapid exchange catheter, as can be done advantageously with OTW catheters. A guide wire can be withdrawn, sometimes unintentionally, from the proximal guide wire port, thus derailing an indwelling rapid exchange catheter. However, neither the first guide wire, nor a replacement guide wire, can be directed back into the catheter's proximal guide wire port, which is hidden remotely in the guiding catheter within the patient.

Guide wires are commonly back loaded into the delivery catheter. In this operation, the guide wire proximal end is inserted into the distal tip of the catheter. It is pushed through the catheter until it extends out of the proximal guide wire exit. In a traditional over-the-wire catheter the proximal guide wire exit is the proximal end of the catheter through its inflation luer. The rapid exchange proximal guide wire exit is the termination of the short guide wire tube a few centimeters or typically 25 centimeters beyond the distal tip of the catheter. In the MX catheter, the proximal guide wire exit is through the guide member positioned on the proximal shaft of the catheter. As an alternative to back loading a guide wire into the delivery system, a guide wire may also be front-loaded. In a front-loading operation, the distal tip of the guide wire is inserted into the guide wire lumen on the proximal shaft and pushed through until it exits the distal tip of the delivery catheter. A front-loading operation is possible with OTW and MX catheters if the guide wire will be exchanged during procedures. A front loading operation is not used with a rapid exchange catheter since the guide wire cannot be exchanged while the catheter is inserted into the patient. With a rapid exchange catheter, the insertion of the distal tip into the proximal end of an indwelling catheter guide wire lumen is pure chance due to the fact that the proximal end is typically 125 centimeters from the exit location of the catheter at the femoral artery in the groin.

The guide member of the MX catheter is used for both advancement of the catheter into the patient and for exchanging the guide wire during the procedure without removing the catheter. In order to further optimize applications of the catheter, it is desirable to increase shaft flexibility while decreasing its size and having appropriate pushability to enable the shaft to advance it through small tortuous distal lesions. A smaller shaft profile also results in greater dye flow though the guide catheter shaft for dye injections used when visualizing the treatment area. However, if the inflation lumen is too small, inflation and deflation times of the balloon could be sacrificed. The transition between the proximal shaft and the distal shaft is an important design consideration. The proximal shaft must provide sufficient stiffness providing pushability to the catheter. The distal section is highly flexibility to track the tortuous distal vessels. The transition between the proximal shaft and distal shaft then becomes a potential kink location if a smooth change from stiffness to flexibility is not achieved. On a MX catheter, the proximal shaft further includes the guide member stop adjacent the transition between the proximal shaft and distal shaft. Thus, design of the transition area must take the stops into consideration.

The present invention is directed towards various embodiments of the proximal shaft that optimizes the proximal shaft profile without sacrificing inflation/deflation times or pushibility of the catheter. Furthermore, the transition between the proximal shaft and the distal shaft of the catheter must be optimized to ensure a smooth transition. It is among the general objects of the invention to provide an improved device that overcomes the foregoing difficulties

SUMMARY OF THE INVENTION

The present invention is a guide member for an MX catheter and guide wire exchange system. The MX catheter and guide wire exchange system comprises an elongate flexible catheter having proximal and distal ends and first and second lumens extending there through. The first lumen is open at the shaft distal end and is sized and shaped to sizably receive a guide wire. The second lumen is sized and shaped to receive inflation fluid therethrough. The catheter has a proximal shaft that may be either bi-lumen or tri-lumen. The shafts may have a generally circular, triangular or shamrock configuration. The inflation lumens in the various proximal shaft embodiments include a hypotube support. In the circular shaft, the inflation lumen and its hypotube have a cresecent shaped configuration while the inflation lumens and their hypotubes used in the oval bilumen shaft and the trilumen shaft are generally circular. The third lumen of the trilumen shaft contains a stiffening wire that extends partially into the distal shaft. The distal end of the stiffening wire is tapered and thus the stiffening wire acts as a transition from stiffer proximal shaft to the more flexible distal shaft. Alternatively, the third lumen may be an additional inflation lumen.

Proximal shaft includes a guide way formed from a longitudinal cut in the shaft wall to enable transverse access to the guide wire lumen. The guide way extends along a major portion of the length of the proximal shaft from a location adjacent to the proximal end of the catheter to a location proximal of the proximal shaft distal end. An enlarged stop is located on the exterior of the proximal shaft distal end and at the distal end of the guide way. A speed bump may be located adjacent the stop. This is positioned such that the guide member is held between the stop and speed bump during wire loading. The distal shaft is preferably coaxial. A balloon is mounted about catheter distal segment, with the balloon being in fluid communication with the inflation lumen.

The distal and proximal shafts are coupled through a transition section. At the transition section, an outer tubular portion of distal shaft overlaps the outer surface of the proximal shaft distal end. Proximal end of distal shaft inner tubular member is positioned within the first lumen of the proximal shaft. The shafts are then fused forming the transition section.

The guide member is mounted on the catheter proximal shaft and its keel is received in a guide way. The guide member has a catheter passageway that extends longitudinally through the guide member and a guide wire passageway for slidably receiving a guide wire therethrough. The guide member keel cooperates with the guide way to assist in merging the guide wire into the first lumen as the catheter shaft is moved through the catheter passageway. Conversely, the guide member can be used for separating the guide wire and catheter by guiding the guide wire out of the guide wire lumen through the guide way. The guide member contains an outer member that rotates freely around the guide member positioned on the catheter shaft. Rotation of the outer member does not affect the position of the guide member keel with respect to the longitudinal cut.

BRIEF DESCRIPTION OF THE DRAWINGS

These and other features, aspects and advantages of the present invention will become better understood with reference to the following description, appended claims, and accompanying drawings where:

FIG. 1 is an illustration of a MX catheter and guide wire in an assembled configuration;

FIG. 1A is a cross-section taken along line A—A of FIG. 1;

FIG. 1B is a cross-section taken along line B—B of FIG. 1;

FIG. 1C is a cross-section taken along line C—C of FIG. 1;

FIG. 1D is a cross-section taken along line D—D of FIG. 1;

FIG. 4A is an end view of a tri-lumen proximal shaft embodiment of the present invention having a shamrock configuration;

FIG. 4B is a perspective end view of a tri-lumen proximal shaft embodiment of the present invention having a shamrock configuration;

FIG. 4C is an end view of a tri-lumen proximal shaft embodiment of the present invention having a triangular configuration;

FIG. 4D is an end view of a tri-lumen proximal shaft embodiment of the present invention having an circular configuration;

FIGS. 8 and 9 are transverse sectional illustrations of the construction of the transition section having a trilumen proximal shaft prior to forming the transition bond;

FIGS. 10 and 11 are transverse sectional illustrations of an alternative embodiment of the transition section having a trilumen proximal shaft prior to forming the transition bond;

Detailed Description of the Invention

Figure 2A:
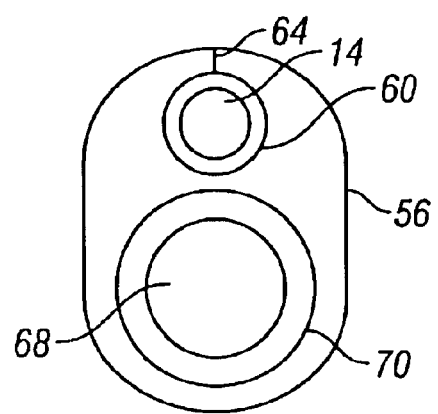
FIG. 2A is an end view of a bi-lumen proximal shaft embodiment of the present invention having an oval configuration.

The present invention is an improved MX catheter 10 shown in FIGS. 1 and 1A–1D. MX catheter 10 includes guide member 12 with guide wire 14 illustrated as extending through guide member 12. Guide member 12 serves as a juncture in which the catheter 10 and guide wire 14 may be merged or separated so that the portion of guide wire 14 which extends proximally of guide member 12 (to the left as seen in FIG. 1) is separated from catheter 10 and the portion of guide wire 14 which is located distally of guide member 12 (to the right as seen in FIG. 1) is contained and housed within catheter 12 except for distal end 16 of guide wire 14 which may protrude distally out of catheter distal end 18. Co-pending patent application titled CATHETER AND GUIDE WIRE EXCHANGE SYSTEM WITH DECOUPLED GUIDE MEMBER and filed concurrently with this application describes various guide member arrangements for MX catheters and is incorporated herein by reference in its entirety.

Catheter 10 includes an elongate, flexible, cylindrical main body having a distal shaft 20 and a proximal shaft 22. In the embodiment shown in FIG. 1, catheter 10 is a delivery catheter, such as for PTCA or stent delivery, having balloon 24 mounted around the catheter body near catheter distal end 18. Balloon 24 may be inflated and deflated through inflation lumen 26 formed through the body of the catheter 10. Inflation lumen 26 extends from the proximal end of catheter 10, where it communicates with fitting 28 and extends the length of catheter 10, terminating in communication with the interior of balloon 24. Fitting 28 may be connected to a suitable source of pressurized fluid or a partial vacuum (not shown) to inflate or deflate balloon 24.

Catheter 10 includes another lumen, indicated at 30, which is intended to receive guide wire 14. Guide wire lumen 30 extends the full length of catheter 10, terminating at distal end 18 and proximal fitting 28. A longitudinal cut extends into the guidewire lumen along the length of proximal shaft 22 forming guide way 32. Guide way proximal end 34 may terminate at or near fitting 28. In the embodiment shown in FIG. 1, guide way distal end 36 terminates short of proximal shaft distal end 38, thereby leaving distal section 40 of proximal shaft 22 in which guide wire lumen is defined by a continuous surrounding wall as shown in FIG. 1B. Inflation lumen 26 encompasses elongate stiffening member 42, which causes the proximal shaft 22 to have greater bending stiffness than guide wire 14. Stiffening member 42 extends at least through the length of catheter 10 that includes guide way 32, thus preventing the shaft from bending such that guide way 32 could buckle. Stiffening member 42 is skived at its distal end portion that extends into distal shaft 20 as shown in FIG. 1C.

Figure 2B:
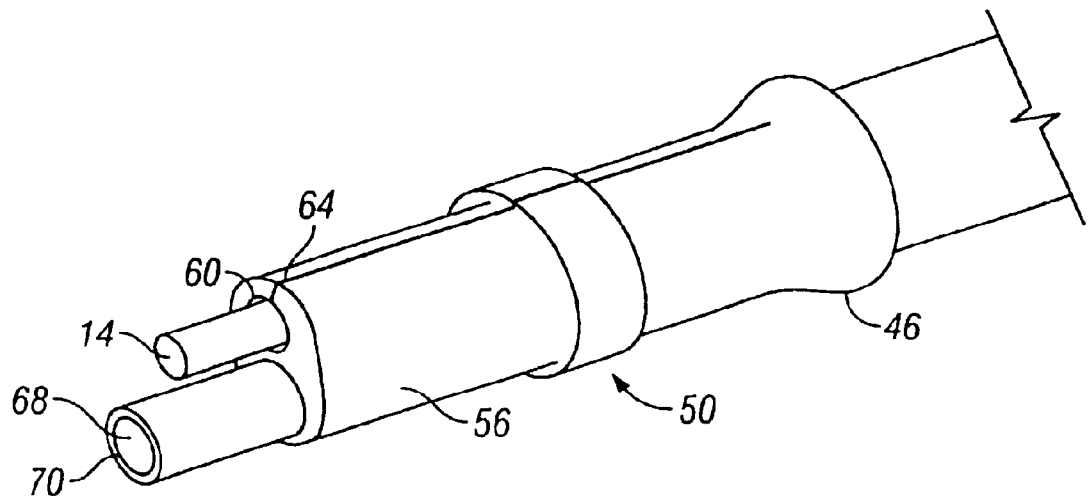
FIG. 2B is a perspective end view of a bi-lumen proximal shaft embodiment of the present invention having an oval configuration.
Figure 3A:
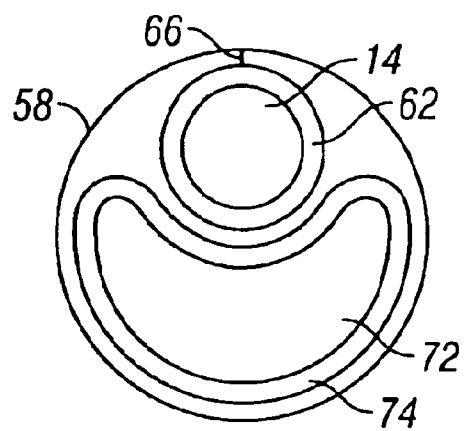
FIG. 3A is an end view of a bi-lumen proximal shaft embodiment of the present invention having a circular configuration.
Figure 3B:
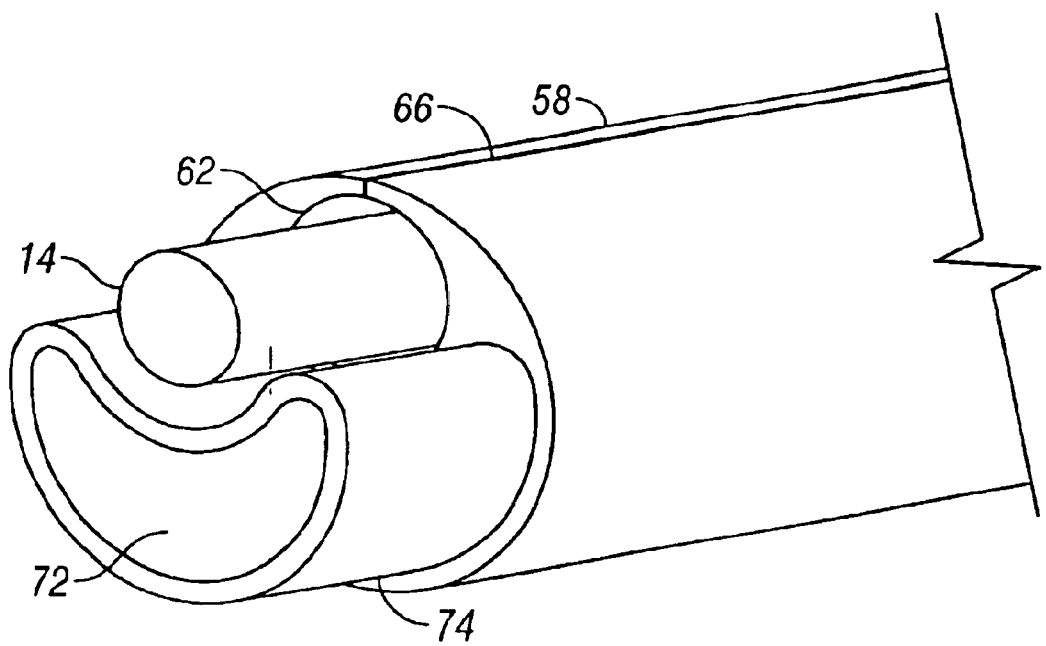
FIG. 3B is a perspective end view of a bi-lumen proximal shaft embodiment of the present invention having a circular configuration.
Figure 12:
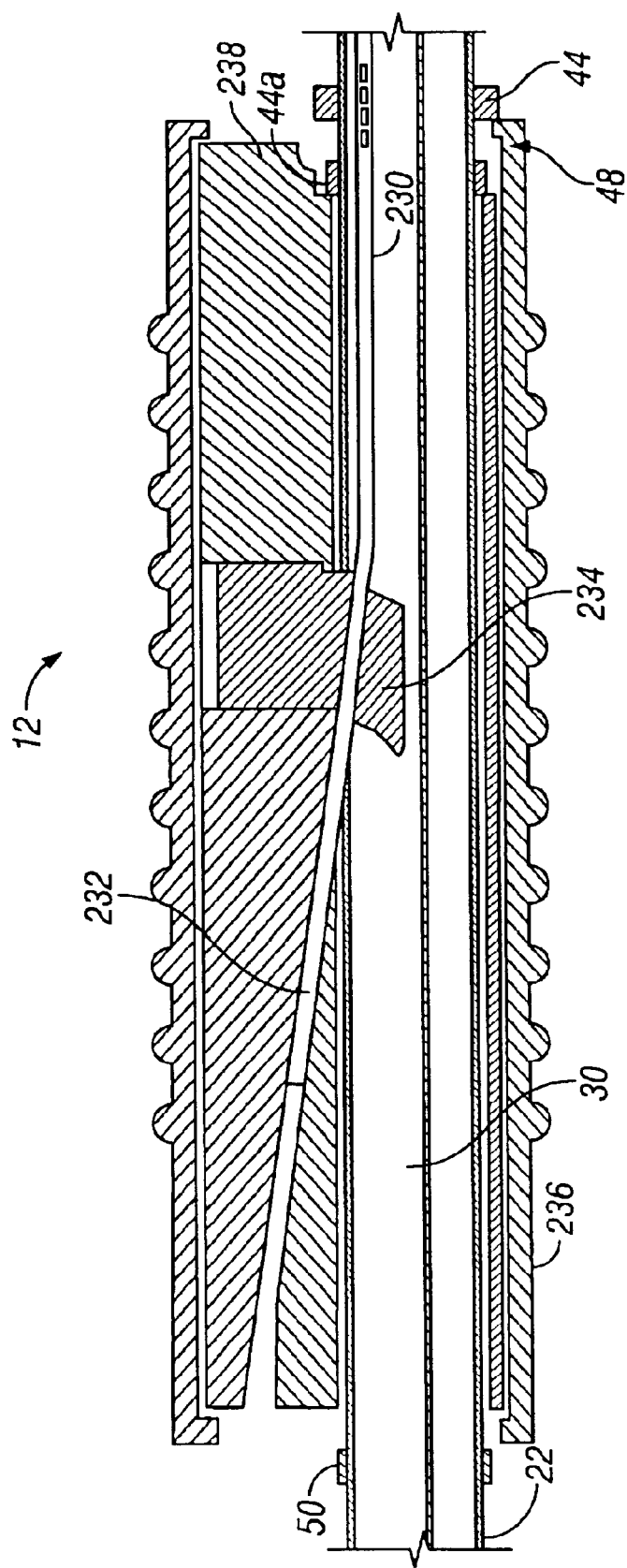
FIG. 12 is a cross section view of the intersection of the guide member and the proximal shaft of the present invention.

Proximal shaft 22 preferably contains stop 44 adjacent its distal end 38. Stop 44 may be an enlarged section of proximal shaft 22 that prevents guide member 12 from traveling onto distal shaft 20. Stop 44 is located approximate guide way distal end 36. Stop 44 is a raised portion on the proximal shaft as seen in FIG. 1. The raised portion may be annular or multiple areas spaced around the shaft circumference such as the two raised areas spaced 180 degrees apart. Stop 44 may act as a wall against which guide member 12 abuts, as in FIG. 1, or an angled ramp 46, as shown in FIG. 2B,against which guide member 12 wedges. Lastly, as shown in FIG. 12, stop 44a may create an interference fit with docking area 48 on guide member 12. Stop 44a is a smaller enlarged area that will be used with stop 44 and helps hold guide member in place on the shaft. A smaller raised area may also be located on proximal shaft 22 to act as a speed bump 50 as seen in FIG. 2B. Like stops 44a and 44, speed bump 50 is an enlarged section of proximal shaft 22. However, speed bump 50 is small to pass through guide member 12 as proximal shaft 22 passes through guide member 12. Speed bump 50 is spaced proximally from stop 44 such that guide member 12 is positioned between stop 44 and speed bump 50 when guide member 12 is in its most distal position on proximal shaft 22. Speed bump 50 lets the practitioner be aware that the guide member 12 and stop 44 are near each other. Speed bump 50 will also hold guide member 12 in its distal position during a backloading operation as will be described in greater detail below.

Distal shaft 20 is preferably coaxial as shown in FIGS. 1C and 1D. Distal shaft has an outer tube 52 forming the inflation lumen 26 and an inner tube 54 forming the guidewire lumen 30. The outer and inner tubes 52 and 54 are arranged in a coaxial configuration. Distal shaft outer tube 52 may likewise be formed from a polyethylene or multi-layer extrusion that has an inner layer that readily fuses with the material of proximal shaft 22. Inner tube 54 may be made from a commonly used catheter multilayer extrusion having a nylon or polyamide block copolymer outer layer, a polyethylene inner layer and an intermediate tie layer.

Figure 6:
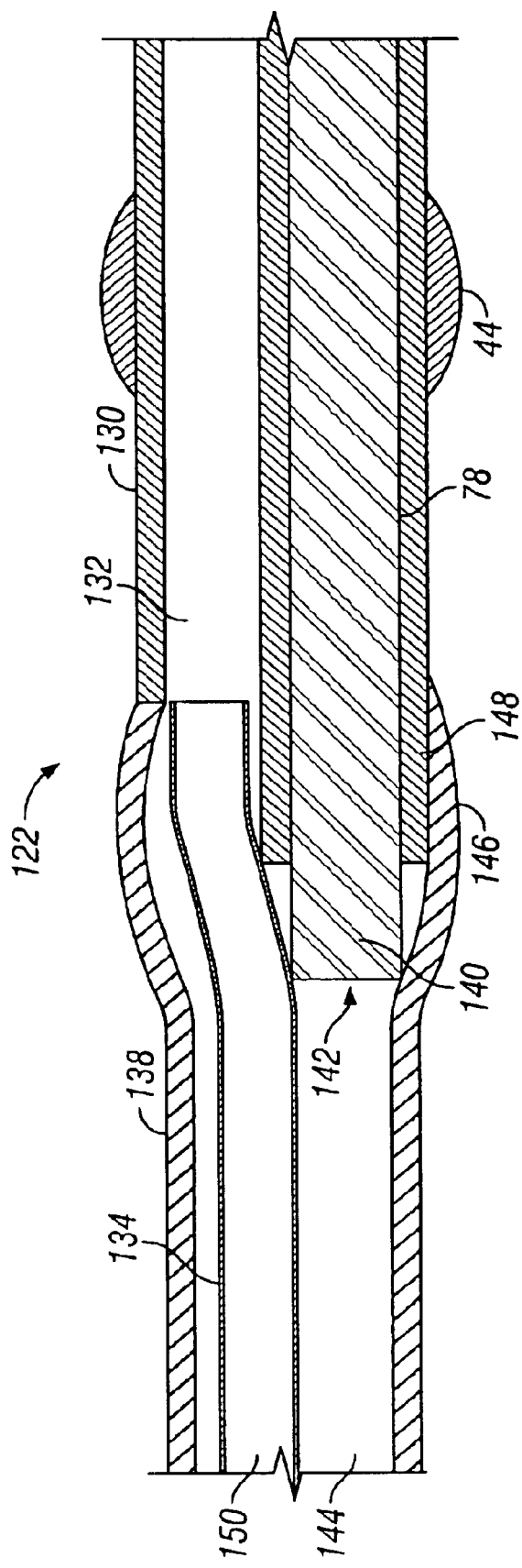
FIG. 6 is a transverse sectional illustration of the construction of the transition section having a bilumen proximal shaft prior to forming the transition bond.
Figure 7:
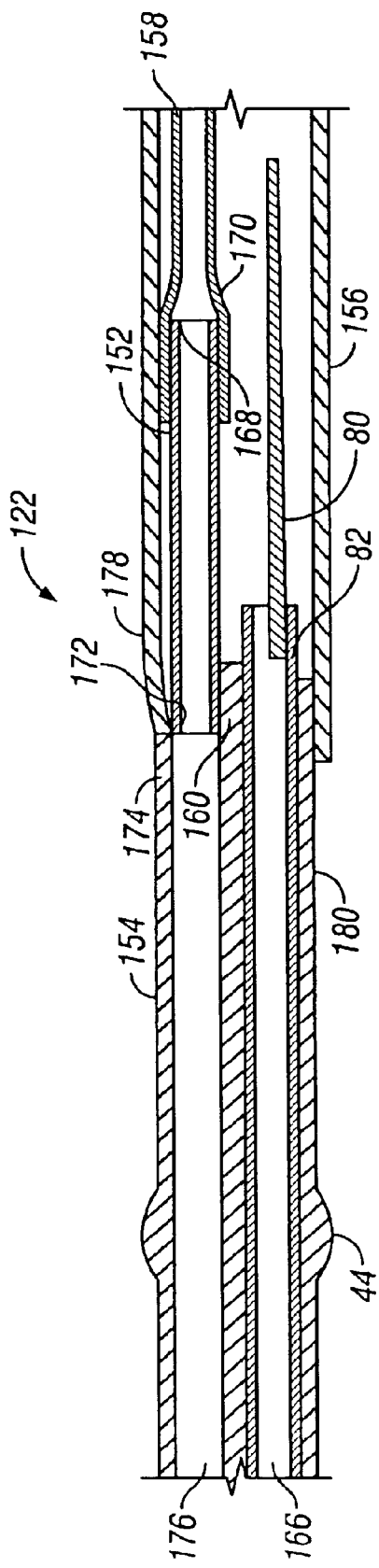
FIG. 7 is a transverse sectional illustration of an alternative embodiment of the transition section having a bilumen proximal shaft prior to forming the transition bond.

Proximal shaft 22 may be a bi-lumen shaft or a tri-lumen shaft. The bi-lumen shaft may be oval or circular as shown by proximal shafts 56 and 58 in FIGS. 2A–3B. Proximal shafts 56 and 58 each have guidewire lumens 60 and 62 that are accessible though guideways 64 and 66 located along the length of the proximal shaft as in the manner shown in FIG. 1. Inflation lumen 68 runs side by side along the length of proximal shaft 56 with guidewire lumen 60 and is preferably supported by a stiffening member 70, such as a hypotube. Inflation lumen 72 of shaft 58 is crescent shaped and also contains a stiffening member 74, such as a crescent shaped hypotube. Stiffening members 70 and 74 provide stiffness for force transmission along the length of the catheter. They may further include a transition section such as a spiral cut distal section 78 as shown in FIG. 6 or a tapered stiffening wire 80 extending from the distal end of the hypotube as shown in FIG. 7. These transition sections ease the transition from the stiffer proximal shaft to the flexible distal shaft and avoid shaft kinking at the proximal shaft 22 and distal shaft 20 junction.

Turning now to FIGS. 4A–D, trilumen shafts 84, 86 and 88 may be generally circular, shamrock shaped or triangular shaped. The lumens are preferably arranged within the shaft in a triangular or shamrock configuration as shown. As shown in FIGS. 4A and 4B guide wire lumen 90 is accessible by guideway 92. Inflation lumen 94 preferably contains a stiffening member 96, such as a hypotube. Third lumen 98 contains a stiffening wire 100. Stiffening wire 100 preferably tapers from stiffer proximal shaft 22 towards more flexible distal shaft 20. Stiffening wire 100 preferably extends into the distal shaft to help transition the catheter from its stiffer proximal shaft 22 to its more flexible distal shaft 20. Stiffening wire 100 may freely float within its lumen, be bonded to the lumen wall at its proximal end, or be bonded to the lumen wall at its proximal and distal end. Stiffening wire 100 is more resistant to kinking than a hypotube since unlike a hypotube, a wire is solid. Stiffening wire 100 is preferably made of stainless steel, tungsten or any other comparable material and is preferable 0.019–0.018" in diameter, with a taper at the distal end portion. The taper may be gradual or in a series of stepped tapers, such as three tapers. Use of the stiffening wire allows use of a thinner and smaller diameter hypotube in the inflation lumen since the tapered wire provides the stiffness and transition previous provided by the hypotube. A conventional delivery system incorporating a hypotube uses a hypotube with a 0.023" outer diameter and a 0.017" inner diameter. A 0.20"×0.17" or 0.0 180'×0.015' hypotube may be used unstead. Trilumen shaft 86 likewise has guideway 102, guidewire lumen 104, inflation lumen 106 with a thinner hypotube 108 and stiffening wire 110 extending through the third lumen. Trilumen shaft 88 has guideway 112, guidewire lumen 114, inflation lumen 116 with a thinner hypotube 118 and stiffening wire 120 extending through the third lumen. Hypotubes 108 and 118, like hypotube 96, can be smaller in diameter with a thinner wall thickness because of stiffening wires 110 and 120.

Proximal shaft 22 is preferably comprised of polyethylene, but other suitable biomedical grade materials such as cross-linked PE, polyolefins, polyamides, blends of polyamides and polyolefins, fluoropolymers, polyesters, polyketones, polyimides, polysulphones, polyoxymethylens and compatibilisers based on polyolefins, included grafted polyolefins and other comparable materials may be used. A lubrication additive may also be used with any polymer and may include PE micro-powders, fluoropolymers, silicone based oils, fluoro-ether oils, molybdenum disulphide and polyethylene oxide. Additionally a reinforcing additive may be used such as nano-clays, graphite, carbon fibers, glass fibres and polymeric fibres.

As described earlier, distal shaft 20 has outer tube 52 forming inflation lumen 26 and inner tube 54 forming guidewire lumen 30 that are arranged in a coaxial configuration. Distal shaft outer tube 52 may be formed from a polyethylene or multilayer extrusion that has an inner layer that readily fuses with the material of proximal shaft 22. Inner tube 54 may be made from a commonly used catheter mutilayer extrusion having a nylon or polyamide block copolymer outer layer, a polyethylene inner layer and an intermediate tie layer.

Figure 5:
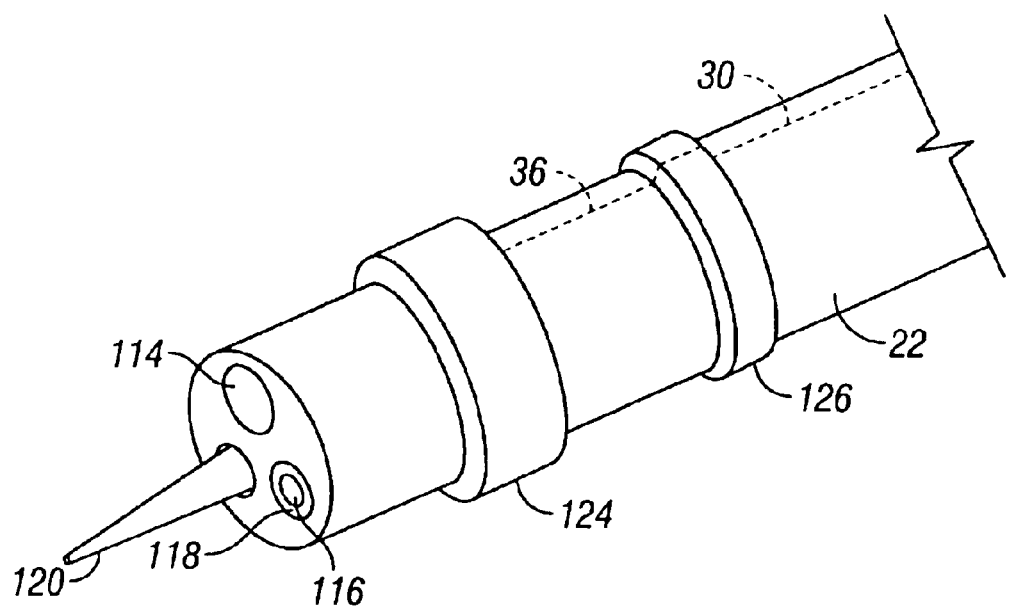
FIG. 5 is an illustration of the construction of the stop member and speed bump of the present invention prior to bonding them to the catheter.
Figure 13:
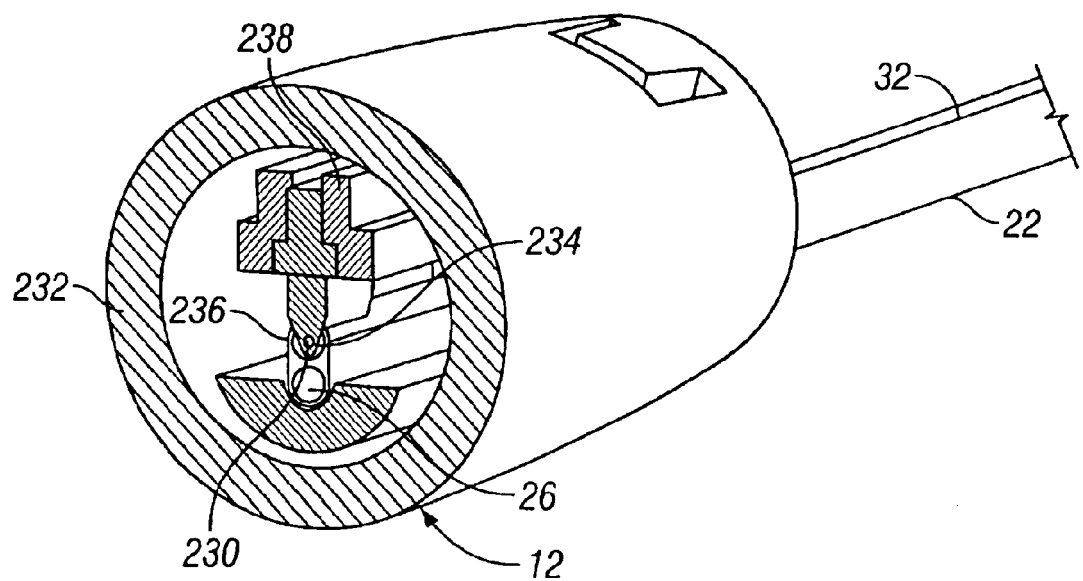
FIG. 13 is a perspective cross-section view of the guide member and the proximal catheter shaft of the present invention.

Catheter 10 transforms from its proximal side-by-side lumen configuration to a distal coaxial configuration adjacent proximal shaft distal end 38 at transition section 122. Prior to forming the transition section 122, stop 44 is formed on proximal shaft 22 as shown in FIG. 5. A tubular member 124, preferably made of polyethylene or other suitable material that may be fused with proximal shaft 22, is placed over proximal shaft distal section 38 and positioned proximate guide way distal end 36. Heat is applied to fuse tubular member 124 to proximal shaft 22. As is well known to those of skill in the art, heat can be applied by any suitable heat source such as a hot air source or a laser source. If speed bump 50 or docking stop 44a will be used on proximal shaft 22, they are formed in the same manner as stop 44. A tubular member 126 is placed over proximal shaft at the desired location and then secured by supplying heat to fuse tubular member 126 to proximal shaft 22. Then to maintain the integrity of guideway, the speed bump 50 must be cut as shown in hidden line so that the guide member may pass therethrough. Stop 44 and speed bump 50 increase the outer diameter of proximal shaft 22 by an amount sufficient to prevent guide member 12 from moving distally past stop 32. If a docking arrangement will be used, docking stop 44a is configured appropriately to mate with docking area 48 on guide member 12. Alternatively, stop 44, speed bump 50 and docking stop 44a may be formed integrally with proximal shaft 22 when it is initially extruded or tubular members 124 and 126 may be secured with an adhesive instead of a heat bond as will be understood by those of skill in the art.

Turning now to FIG. 6, the formation of transition section 122 will be described for the bi-lumen proximal shafts. As shown, after stop 44 has been positioned on proximal shaft 22, proximal shaft portion 130 adjacent guide wire lumen 132 is cut back, preferably at an angle, along a portion of its wall. Distal shaft inner tube 134 is placed adjacent proximal shaft guide wire lumen 132 within the cut area. Proximal shaft 130 contains stiffening member 78 that is preferably a hypotube with a spiral cut distal section 140 to assist in providing a smooth transition from proximal shaft 130 to distal shaft 138. Hypotube distal section 140 extends from proximal shaft inflation lumen 142 and is inserted into distal shaft inflation lumen 144. Outer tube proximal end 146 is positioned to overlap proximal shaft distal end 148. The amount of overlap is preferably minimal such as 3 to 6 mm. Mandrels (not shown) are inserted into guide wire and inflation lumens 132, 142, 144 and 150 to prevent closure of the lumens during application of heat for bonding. While any appropriate heat source may be used, application of laser heat is preferred for forming a fusion bond that is minimal in size to avoid creating a potential kink point in the catheter while also being fluid tight and able to withstand the necessary pressures in a catheter procedure. Alternatively, other bonding methods may be used such as use of an adhesive.

FIG. 7 shows an alternative embodiment for transition section 122 that incorporates a connecting tube 152. In this embodiment, proximal shaft 154 may be formed from a commonly used catheter material, such as polyethylene. Distal shaft outer tube 156 may likewise be formed from a polyethylene or multilayer extrusion that has an inner layer that readily fuses with the material of proximal shaft 154. Distal shaft inner tube 158 may be made from a commonly used catheter multilayer extrusion having a nylon or polyamide block copolymer outer layer, a polyethylene inner layer and an intermediate tie layer. The nylon or polyamide block copolymer outer layer of inner tube 158 will not readily bond to the polyethylene of proximal shaft 154. Connecting tube 152 is preferably made of polyethylene and is used to assist in bonding distal inner tube 158 with the inner surface of guide wire lumen 176 to form a fluid tight seal necessary for the integrity of overall catheter inflation lumen 166. Connecting tube distal end 168 is placed within proximal end 170 of distal inner tube 158. Proximal end 172 is inserted into guide wire lumen distal end 174 which may be cut back along a portion of its wall as shown. Proximal end 178 of outer tube 156 placed over distal end 180 of proximal shaft 154. The bonding process to form the transition section can then proceed as described above by inserting mandrels and applying appropriate heat.

Formation of the transition section for the tri-lumen proximal shafts is similar to that for the bi-lumen proximal shafts. As shown in FIGS. 8 and 9, proximal shaft portion 182 adjacent guide wire lumen 184 is cut forming area designated 186 to assist in the assembly of catheter 10. Distal shaft inner tube 188 is inserted along area 186 and abuts shaft portion 182 such that when bonded, a fluid tight seal is formed. Proximal shaft inflation lumen 190 contains hypotube 192 that terminates approximate proximal shaft distal end 194. Stiffening wire 196 extends from third lumen 198 into inflation lumen 200 formed by distal shaft outer tube 202 and is tapered to assist in forming a smooth transition from proximal shaft 182 to distal shaft 204. Outer tube proximal end 206 is positioned to overlap proximal shaft distal end 194. The amount of overlap is preferably the minimal such as 3 to 6 mm. Mandrels (not shown) are inserted into guide wire and inflation lumens 184, 190, 200 and 208 to prevent closure of the lumens during application of heat for bonding the shafts. Distal shaft end 194 will shrink around stiffening wire 196 to securely bond it in position. An additional tube (not shown) may be placed over the stiffening wire at the bond location to fill any gaps created around the stiffening wire and maintain the integrity of the bond. Stiffening wire will extend past the bond and into distal shaft 204. Alternatively, a mandrel may also be placed in third lumen 198 during the bonding process if it is not desirable to bond stiffening wire to transition section 122. While any appropriate heat source may be used, application of laser heat is preferred for a forming a fusion bond that is minimal in size to avoid creating a potential kink point in the catheter while also being fluid tight and able to withstand the necessary pressures in a procedure. Alternatively, other bonding methods may be used such as use of an adhesive.

FIGS. 10 and 11 show an alternative embodiment for transition section 122 that incorporates a connecting tube 210 in a trilumen proximal catheter arrangement. In this embodiment, proximal shaft 182 may be formed from a commonly used catheter material, such as polyethylene. Distal shaft outer tube 202 may likewise be formed from a polyethylene or multilayer extrusion that has an inner layer that readily fuses with the material of proximal shaft 182. Distal shaft inner tube 188 may be made from a commonly used catheter mutilayer extrusion having a nylon or polyamide block copolymer outer layer, a polyethylene inner layer and an intermediate tie layer. The nylon or polyamide block copolymer outer layer of inner tube 188 will not readily bond to the polyethylene of proximal shaft 182. Connecting tube 210 is preferably made of polyethylene and readily bonds with the surface of inflation lumen 190 and the inner surface of mulitlayer distal shaft inner tube 188 to form a fluid tight seal necessary for the integrity of overall catheter inflation lumen 26. Connecting tube distal end 212 abuts proximal end 214 of inner tube 188. Proximal end 216 is placed adjacent distal end 218 of guidewire lumen 184 along area 186 created by cutting back a wall portion of proximal shafr 182. Proximal end 206 of outer tube 202 is inserted over distal end 194 of proximal shaft 182. The bonding process to form the transition section can then proceed as described above by using mandrels and application of a heat source.

With reference now to FIGS. 1, 2B, 12 and 13, operation of the device will now be described. Once the guide wire 14 and guide catheter (not shown) are inserted into the patient, catheter 10 is inserted with a backloading operation. Guidewire 14 is inserted into distal end 18 of catheter 10 and threaded proximally through guide wire lumen 30 until guide wire tube 230 captures proximal end of guidewire 14 and directs it into passageway 232 and then out of guide member 12 as shown in FIG. 1. This procedure is typically accomplished with the guide member 12 adjacent the guide way distal end. The guide member 12 may be positioned between stop 44 and speed bump 50. This will keep guide member in proper position during the backloading postion as the force of the wire entering the guide member is insufficient to push the guide member 12 proximally over speed bump 50. Alternatively, if the docking area 48 is used to receive stop 44a, the guide member 12 will be held in its distal position when the docking arrangement is engaged. As distal shaft 20 enters the patient, guide member will reach the hemostatic valve (not shown). Guide member 12 is not intended to enter the valve and is seated adjacent the valve. Proximal shaft 22 is then moved through guide member seated against the valve. As proximal shaft is advanced, keel 234 engages guide way 32. Outer member 236 of guide member 12 rotates with respect to the inner body 238. Thus, rotation of outer member 236 will not affect the position of keel 234 with respect to guideway 32 since keel 234 is secured to inner body 238.

Once inserted, the hemostatic valve may be closed down on the catheter shaft distal of guide member 12. If a wire change is required, one simply withdraws guide wire 14 from guide member 12 as it is seated against the valve and proximal shaft remains in the patient. A new guide wire is then inserted into the catheter through passageway 232 on guide member 12. If a catheter exchange is required, one simply holds the wire in place and begins moving proximal shaft 22 proximally though guide member 12 which is kept at the hemostatic valve. Once stop 44 on proximal shaft 22 is reached, the remaining portion of the catheter is removed while guidewire 14 is still held in place with respect to the lesion site. Another catheter may then be backloaded onto guide wire 14 and introduced into the patient as described above.

While the invention has been particularly shown and described with reference to the preferred embodiments thereof, it will be understood by those skilled in the art that various changes in form and detail may be made there in without departing from the spirit and scope of the invention.

What is claimed is:

1. A catheter and guide wire exchange system comprising:
   an elongate flexible catheter shaft having proximal and distal shafts, the proximal shaft contains a tri lumen arrangement of tubes defining a first guide wire lumen and first inflation lumen and a stiffening wire lumen, the distal shaft contains a coaxial arrangement of an inner tube defining a second guide wire lumen and an outer tube surrounding the inner tube thereby defining second inflation lumen;
   a longitudinal guide way formed in the proximal shaft to enable transverse access to the first guide wire lumen through the proximal shaft, the guide way extending along a major portion of the length of the proximal shaft from a location adjacent a proximal end of the proximal shaft to a distal terminal end proximal of a distal end of the proximal shaft, thereby defining an uncut distal segment of the proximal shaft;
   a stop located on the proximal shaft at the distal terminal end of the guide way;
   a speed bump located on the proximal shaft proximal of the stop;
   a balloon mounted about a distal segment of the distal shaft, the balloon being in fluid communication with the second inflation lumen;
   a guide member mounted on the proximal shaft and having a catheter passageway extending there through for slidably receiving the catheter shaft and a guide wire passageway for slidably receiving the guide wire for merging the guide wire and the catheter by guiding the guide wire transversely through the guide way and into the first guide wire lumen and for separating the guide wire and catheter by guiding the guide wire transversely out of the first guide wire lumen through said guide way; and a transition segment between the proximal shaft and the distal shaft, the transition segment comprising the proximal shaft having a cut back section adjacent the first guide wire lumen at its distal end and a non cut back section at its distal end, the distal shaft outer tube abutting the proximal shaft at the cut back section and overlapping the non cut back section of the proximal shaft distal end and the distal shaft inner tube inserted in the first guide wire lumen in the proximal shaft.

2. The catheter and guide wire exchange system of claim 1, wherein the guide member has at least one keel disposed within the catheter passageway and being adapted to open and to protrude through the guide way into the first guide wire lumen.

3. The catheter and guide wire exchange system of claim 1, wherein the guide wire passageway extends through a tubular member extending into the catheter passageway and being shaped and sized to fit within the first guide wire lumen.

4. The catheter and guide wire exchange system of claim 1, wherein the first guide wire lumen has a ramp adapted to receive and direct a guide wire proximal end through the guide wire passageway.

5. The catheter and guide wire exchange system of claim 1, wherein the first guide wire lumen has a recess adapted to receive and direct a guide wire proximal end through the guide wire passageway.

6. The catheter and guide wire system of claim 1 wherein the inner tube includes a connecting tube segment positioned between the distal shaft inflation lumen and the proximal shaft inflation lumen, the connecting tube segment having a proximal end for insertion into the first inflation lumen.

7. The catheter and guide wire exchange system of claim 1 wherein the balloon is a stent delivery balloon.

* * * * *